United States Patent [19]

Pietsch et al.

[11] Patent Number: 4,486,488

[45] Date of Patent: Dec. 4, 1984

[54] COMPOSITION FOR THE PRODUCTION OF BANDAGES, BANDAGES PRODUCED THEREWITH AND METHOD FOR THE PRODUCTION THEREOF

[75] Inventors: Hanns Pietsch, Hamburg; Volker Hohmann, Norderstedt, both of Fed. Rep. of Germany

[73] Assignee: Beiersdorf Aktiengesellschaft, Hamburg, Fed. Rep. of Germany

[21] Appl. No.: 476,042

[22] Filed: Mar. 17, 1983

Related U.S. Application Data

[63] Continuation of Ser. No. 262,147, May 11, 1981, abandoned.

[30] Foreign Application Priority Data

May 17, 1980 [DE] Fed. Rep. of Germany ....... 3018969

[51] Int. Cl.³ .................... B65B 55/02; A61F 13/00; B32B 7/02
[52] U.S. Cl. .................. 428/219; 53/111 R; 53/425; 106/189; 106/193 R; 128/155; 128/156; 424/362; 424/145; 424/28
[58] Field of Search ............... 106/189, 193; 128/155, 128/156; 424/145, 28, 362; 428/219

[56] References Cited

U.S. PATENT DOCUMENTS

| | | | |
|---|---|---|---|
| 1,895,367 | 5/1933 | Bernhard | 106/193 |
| 2,833,661 | 5/1958 | Iler | 106/193 J |
| 3,043,298 | 7/1962 | Brickman | 128/91 |
| 3,122,479 | 2/1964 | Smith | 106/197 R |
| 3,328,259 | 6/1967 | Anderson | 424/150 |
| 4,166,744 | 9/1979 | Smith | 106/35 |

FOREIGN PATENT DOCUMENTS

| | | |
|---|---|---|
| 1282228 | 11/1968 | Fed. Rep. of Germany . |
| 1767434 | 5/1972 | Fed. Rep. of Germany . |
| 1227448 | 8/1960 | France . |
| 282212 | 4/1982 | Switzerland . |
| 498975 | 1/1979 | United Kingdom . |

*Primary Examiner*—Theodore Morris
*Attorney, Agent, or Firm*—Jordan B. Bierman

[57] ABSTRACT

A composition which is particularly useful in semi-rigid medical supporting bandages comprising 10 to 35% zinc oxide
2 to 15% cellulose ether
10 to 35% glycerin
30 to 75% water.

The composition is coated onto at least one side of a suitable substrate to form the bandage and is irradiated in order to preserve sterility. Preferably, the radiation would take place after the bandages have been packaged.

28 Claims, No Drawings

COMPOSITION FOR THE PRODUCTION OF BANDAGES, BANDAGES PRODUCED THEREWITH AND METHOD FOR THE PRODUCTION THEREOF

This application is a continuation of Ser. No. 262,147, filed May 11, 1981 which now abandoned claims the priority of German Application P 30 18 969.6, filed May 17, 1980.

The present invention is directed to a composition which is particularly suitable for the production of semi-rigid dressings for medical purposes, bandages made therefrom, and the production of the latter.

In the past, zinc oxide dressings have been known. They consist of zinc oxide, glycerin, water, and a preservative. A number of other natural substances, such as gelatin, alginates, gum arabic, and agar agar, are also added as binders. The glycerin can be partly replaced by other polyvalent alcohols, such as 1,2-propyleneglycol or sorbitol. The preservatives are commonly esters of p-hydroxybenzoic acid or boric acid.

Bandages of the foregoing description have been used for many years in the treatment of leg injuries or disorders. They are used in the treatment of thromboses, for the healing of leg ulcers, as a supporting dressing in minor injuries, to prevent swelling of broken limbs after removal of the plaster cast, and as semi-rigid compression dressings in cases of varicosis, ulcers, phlebitis, and leg edema.

These bandages have certain advantages and disadvantages. Among the former is the fact that they are extremely gentle to the skin, and actually have a nursing and healing effect thereon.

On the other hand, such bandages take a long time to dry after application. As a result, they are sticky and greasy for a substantial period until they can finally dry out. Moreover, there are a number of patients (whose number is constantly increasing) who do not tolerate the preservatives contained in these bandages and evidence substantial skin irritations. Indeed, these irritations would not only obviate the known gentleness and curative effect on the skin of these dressings, but would also create worse conditions than would result from the use of a neutral bandage. For these reasons, a number of physicians advise against the use of zinc oxide in this context.

In order to minimize the foregoing undesirable effects, the amount of preservative is kept as low as possible. When this is done, it repeatedly occurs that the moist bandage becomes contaminated by bacteria or fungi, especially on prolonged storage or due to inadequate packing. Such contamination is evidenced by an unpleasant odor and unsightly appearance. In particular, the decomposition of gelatin results in an odor which is a combination of ammonia and amines. Such a disagreeable smell is frequently found in commercial products to varying degrees, depending on the particular product and the storage time and conditions.

An effective and simple method of killing such microorganism si the application of energy-rich radiation, such as beta or gamma rays. When compared to gas sterilization, it has an important advantage in that sterilization can be carried out even after the product has been packaged. This is of particular value when the bandages are packaged in gas-tight (hence water vapor-impermeable), germ proof, hermetically sealed material; e.g. glass or metal. Obviously, subsequent contamination is not possible when sterilization is carried out in this manner. When this method is compared to steam sterilization, it has the advantage that the bandage is not subjected to high temperatures and the possibility of deterioration which might very well result.

However, a number of materials, including the natural binders, are altered by the action of the energy-rich rays in normal sterilization doses. For example, an aqueous gelatin gel will coagulate on radiation. Gum arabic develops an unpleasant, slightly pungent odor after gamma radiation. With other natural binders, there is frequently a substantial drop in viscosity.

As a result of the foregoing, the traditional zinc oxide pastes (which contain gelatin and/or other admixtures of natural binders) cannot be sterilized by radiation. The coagulation of the gelatin, accompanied by separation out of water, prevents molding of the bandage when it is sought to be applied. The ability to be molded is absolutely necessary for the proper application of such bandages in order to prevent undue pressure being exerted at various points on the portion of the body being bandaged.

A further disadvantage of the known zinc oxide paste is that heating is necessary in order to dissolve the gelatin in the water before the other components are added. While this problem is far from insuperable, it is a definite drawback as part of an economic manufacturing procedure.

Therefore, it is among the objects of the present invention to provide a composition containing zinc oxide, bandages made therefrom, and a simple method for the production thereof without the aforementioned disadvantages.

It is also among the objects of this invention to provide a bandage which dries rapidly after application, and exhibits better skin tolerance.

It is also among the objects of this invention to provide a bandage which is simpler and easier to sterilize than those of the prior art.

Such bandages should not undergo any deleterious changes during treatment with energy-rich rays, and the compositions of which the bandages are composed should have a creamy consistency so that they can be readily molded when applied to the human body. This will result in an excellent fit and a smooth dressing. It is also of advantage to produce the composition and bandage at a low temperature in conventional coating plants. Similarly, the sterilization by radiation should also be carried out in the conventional manner.

It has been found that these problems can be solved or minimized by a bandage made from a composition which comprises 10–35% zinc oxide
2–15% cellulose ether
10–35% glycerin
30–75% water.

Of course, up to at least 5% of the usual additives can be included in this composition. Preferably, the composition comprises 10–20% zinc oxide
3–5% cellulose ether
10–20% glycerin
60–70% water.

All percentages are by weight.

It is particularly preferred to sterilize either the compositions or bandages made therewith by the use of energy-rich rays; such as beta rays or gamma rays.

The zinc oxide used is a fine-grained powder, preferably of pharmaceutical quality. For example, that which has been approved by the German Pharmacopoeia is suitable. However, commercially available material such as that generally sold under the name "Weissiegel" is also useful.

The ethers are broadly alkyl ethers, arylalkyl ethers, hydroxyalkyl ethers, and hydroxyalkyl-alkyl ethers, all of cellulose. Preferred ethers are methyl cellulose, ethyl cellulose, benzyl cellulose, ethylmethyl cellulose, hydroxymethyl cellulose, hydroxyethyl cellulose, hydroxypropyl cellulose, hydroxypropylmethyl cellulose, hydroxyethylmethyl cellulose, as well as ethylhydroxyethyl cellulose and hydroxypropylethyl cellulose. Especially preferred are methylhydroxyethyl cellulose, methylhydroxypropyl cellulose, ethylhydroxyethyl cellulose, and hydroxypropylmethyl cellulose. These ethers can be used separately or in mixtures of two or more.

The foregoing ethers are available in various types, differing primarily in their average molecular weight and their viscosity in aqueous solution. In order to characterize their viscosity, a 2% aqueous solution is normally used. Cellulose ethers which are suitable exhibit a viscosity of 50 to 50,000 mPas. in such solution at room temperature. Preferably, the viscosity should be in the range of 50 to 12,000 mPas. Particularly preferred are those which have a viscosity of approximately 2,000 mPas.

If the most preferred ethers (having a viscosity of approximately 2,000 mPas.) are used, it has been found that best results are obtained with 3 to 5% ether present. Smaller quantities will be enough if the viscosity is higher and larger quantities are necessary when the viscosity is lower. At the same time, it must be considered that a viscosity drop will occur after irradiation of the completed mixture or bandages with the energy-rich rays.

It is to be preferred that the viscosity of the compositions in accordance with this invention be from 1 to 100 Pas. The same range applies to those compositions which have already been irradiated.

Suitable additives include additional hydrophilic, macromolecular substances; such as polyvinyl alcohol, polyvinyl pyrrolidone, or polyhydroxyethylmethacrylate; polyethylene oxide, dyes, perfumes, preservatives, or inorganic thickeners; such as silicates or silicon dioxide. These inorganic, finely-divided thickeners impart very desirable thixotropic properties to the compositions and the bandages.

In a preferred form of the invention, the composition contains silicates or highly-dispersed silicon dioxide. The latter should, most preferably, have a BET surface of 100 to 400 $m^2/g$ and a bulk density of approximately 60 g/l. It has been found most advantageous to use from 2 to 4% of the inorganic thickener.

These thickeners are particularly useful to compensate for the visocisity drop caused by radiation. As a result, the use of higher viscosity cellulose ethers can frequently be avoided.

The viscosity of the composition can also be modified by varying the water and zinc oxide contents. The viscosity rises as the water is reduced or the amount of zinc oxide is increased.

The compositions of the present invention are easily prepared by dissolving and stirring the components in water at room temperature. It has been found more advantageous to add the zinc oxide and cellulose ether to the water-glycerin mixture. It is best to introduce the additives (such as the inorganic thickeners) to the liquids first.

The bandages are produced by coating a substrate on one or both sides with the aforementioned composition. Ordinary substrates such as gauze, woven fabrics, and non-woven fabrics are all suitable. The mixture containing the zinc oxide penetrates into the spaces of the substrates quite satisfactorily. Normally, such bandages would be wound onto rolls for easy packaging and subsequent dispensing.

The gauze which is useful can advantageously be that described in DIN No. 61631, with either 20 or 24 threads. Preferably, selvages on both sides should be provided and the warps and wefts are most desirably of cotton/cotton, staple rayon/cotton, or staple rayon/staple rayon. They may be bleached, unbleached, or dyed. It is also possible to use gauze bandages made of other textile yarns; e.g. synthetic fibers, such as polyester, polyamide, viscose, or blended fibers. Moreover, elastic fabrics, which are stretchable longitudinally, transversely, or both are also suitable.

The reason for the two sided selvages is so that the cut warps do not form beads at the edges when the bandages are unwound. Alternatively, the warps and wefts should be fixed by suitable impregnation at the intersections thereof.

It has been found most suitable that the width is 5 to 15 cm, preferably 7 to 10 cm. To aid in easily unwinding the bandages, the outside diameter of the core should be 5 to 20 mm, preferably 8 to 15 mm. It has been found helpful if the edges have slightly rounded beads. The material of the core may be any suitable substance, and cardboard or plastic has been found acceptable. The cardboard should not contain any bleeding dyes or it should be protected by some sort of a coating to prevent such bleeding or softening. The coating could be varnish, foil, or the like.

To assist in finding the end of the bandage, it is useful to attach a tongue or tab, preferably of plastic or impregnated paper. For example, a PVC foil or siliconized paper has been found useful. Such a tab can be 1 to 2 cm wide and 2 to 5 cm long. Preferably the tongue or tab is colored.

In order to store the composition and/or bandages of the present invention, protection from drying out and from germination of microorganisms must be provided. This means that the packaging should be both moisture proof and germ proof. Suitable materials are fusible aluminum foils, such as polyethylene-coated or polypropylene-coated foils, as well as rigid containers, such as cans or boxes of metal, glass, or composite materials. Insofar as the latter is concerned, the covers must, of course, be sealable as, for example, by adhesive tapes.

The production of the bandages themselves is carried out in known manner by applying the composition of the present invention to one or both sides of the substrate. In a preferred embodiment, gauze bandages of suitable width are coated with 120 to 200 $g/m^2$, formed into rolls, and packaged in a moisture proof container.

It is altogether surprising that the zinc oxide formulations of the present invention exhibit the improved characteristics which have been found. The cellulose ethers, which form an important component of the present composition, do not have the typical property of temperature-dependent sol-gel transformation of gelatin. This is accompanied by a great variation in viscosity and which was, heretofore, thought to be obligatory. Therefore, such cellulose ethers were previously considered to be useless in bandages of the present type. In spite of this difference in behavior, it is possible to produce the improved and superior semi-rigid bandages in accordance with the present invention.

A further important advantage of the present invention is the increased drying rate. Within about one to two hours after application, the dressings are well dried, at least on the surface, are mechanically stable, and are no longer sticky.

Moreover, the composition and bandages of the present invention have a lower sensitivity to microorganisms. This manifests itself in improved stability. Moreover, there are no unpleasant odors resulting from aging and storage. The stability is so markedly improved, it is possible to eliminate preservatives completely for shorter storage periods. Products which can be stored for longer periods of time can be obtained by the addition of preservatives, but the amounts required are substantially lower than in the known zinc oxide pastes. In this way, the curative action of the zinc oxide, as well as the tolerance of the skin therefore, is heightened and improved.

It is also no longer necessary to heat any of the components in order to prepare the compositions and, of course, sterilization by energy-rich radiation is extremely desirable to promote sterility in a simple and economic manner.

Thus, in a particularly preferred embodiment of this invention, preservatives are entirely absent from the composition. The mixture (or the bandage produced therefrom) is subjected to treatment with energy-rich rays. While beta and gamma rays are preferred, it is the latter which are most desirable. It has been found advantageous to use cobalt 60 as the radiation source and to provide from 0.5 to 5.0 megarad, preferably 2.5 megarad. The viscosity drop which is caused by the radiation can be compensated for by the previously described measures, especially by the addition of inorganic thickeners.

It has been found that the irradiated compositions, particularly those with the preferred viscosity of 1 to 100 Pas., exhibit a very pleasant, creamy consistency, which facilitates the molding of the applied mixtures or bandages to the body. Of course, the mixtures and bandages have suitable consistency when they have not been irradiated.

Known zinc oxide pastes cannot be irradiated in this manner since the gelatin coagulates and water separates out. The cohesion of the entire mixture is lost so that they can no longer be processed or used.

The gamma radiation is preferably carried out at a level of approximately 2.5 megarad, which is sufficient for the sterilization of either the compositions or the finished bandages. Preservative-free products are obtained by packaging either the composition or the desired bandages in moisture proof and germ proof containers, followed by radiation sterilization as set forth above. It is preferable that the compositions and/or bandages be irradiated not later than three days after production thereof.

The following examples are intended to illustrate the present invention:

EXAMPLE 1

Into 400 g deionized water is introduced 90 g of glycerin. (99%, DAB 8). Then, 90 g of pharmaceutical quality zinc oxide and 20 g of methylhydroxyethyl cellulose (having a viscosity of 2,000 mPas. in 2% aqueous solution at room temperature) are added.

The final composition contains 15% zinc oxide, 3.33% cellulose ether, and 15% glycerin.

160 g/m² of the above composition is applied, in a conventional coating plant equipped to process highly viscous materials, to a gauze bandage 10 cm wide and having 20 threads. The substrate has a selvage on both sides and the resultant coated product is wound on a polystyrene core having 10 mm inside diameter and 14 mm outside diameter, wrapped in wax paper, and wrapped in polyethylene coated aluminum foil which is then fused. Such bandages can be easily processed after storage for several days at room temperature and, even after this period of time under these conditions, evidences no unpleasant odor.

One group of the bandages is irradiated with 2.5 megarad. (cobalt 60) gamma radiation. The other receives no irradiation. The bandages are then stored at both 22° C. and 40° C. for a period of three months. It is found that the irradiated bandages in accordance with the present invention exhibit no decomposition odor or visible fungus attack. The bandages appear to be in all respects satisfactory and suitable for medical use. Moreover, they all have a pleasant, creamy consistency.

On the other hand, the unirradiated bandages all contain circular fungus areas where microorganisms are germinated and flourish. Some are attacked less strongly than others. Those which received the lesser attack had no undesirable odor, and those which are strongly attached had a damp, cellar-type smell.

EXAMPLES 2-5

In accordance with the method as set forth in Example 1, the following compositions are prepared and bandages are formed therefrom.

240 g zinc oxide (pharmaceutical grade)
90 g cellulose ether
270 g glycerin (99% DAB 8)
1200 g deionized water As the cellulose ether the following are used.

| Example | Cellulose Ether | Viscosity of 2% Solution (room temperature) |
|---|---|---|
| 2 | ethylhydroxyethyl cellulose | 50 mPas |
| 3 | " | 300 mPas |
| 4 | " | 700 mPas |
| 5 | hydroxypropylmethyl cellulose | 50 mPas |

The resulting bandages are, as in Example 1, divided into two groups. One group is not irradiated, and the other is irradiated with 2.5 megarad gamma rays. The storage conditions are the same as in Example 1, and the results are also the same. After only two weeks, the unirradiated samples show microorganism (fungus) growths, even at 22° C. On the other hand, the irradiated samples are all in excellent condition, including those which are stored at 40° C. for three months.

In order to judge the suitability of these bandages for their intended use, they are wound on a model leg. After 90 minutes, the bandage surfaces leave no residues when touched by hand, indicating that the bandage was dry on its surface.

EXAMPLES 6-12

In accordance with Example 1, the following compositions are prepared.

268.2 g zinc oxide (pharmaceutical grade)
60 g cellulose ether
270 g glycerin (99% DAB 8)
1200 g deionized water
18 g highly dispersed silicon dioxide (bulk density 60 g/l, BET surface 200 m²/g).

The silicon dioxide is added at the beginning. As cellulose ethers the following are used

| Example | Cellulose Ether | Viscosity in 2% Solution (at room temperature) |
| --- | --- | --- |
| 6 | methylhydroxypropyl cellulose | 1000 mPas |
| 7 | methylhydroxypropyl cellulose | 2000 mPas |
| 8 | methylhydroxypropyl cellulose | 10000 mPas |
| 9 | methylhydroxypropyl cellulose | 30000 mPas |
| 10 | ethylhydroxyethyl cellulose | 2000 mPas |
| 11 | ethylhydroxyethyl cellulose | 7000 mPas |
| 12 | ethylhydroxyethyl cellulose | 12000 mPas |

As in the previous Examples, one group of bandages is irradiated with 2.5 megarad gamma rays and the other is left without such treatment. They are stored under the same conditions as in Example 1 and the results are the same. All of the irradiated samples are in excellent condition even after three months at 40° C., while the unirradiated samples show microorganism colonies even after only two weeks at 22° C.

The bandages are applied to a model leg and evidence excellent, creamy, smooth molding behavior. Within 60 to 90 minutes after application, they were dry on the surface.

EXAMPLES 13-16

Compositions are prepared in accordance with Example 2, with the following components included.

| Example | Zinc Oxide in % | Highly Dispersed SiO$_2$, in % | Polyethylene Oxide[1] in % | Viscosity (Pas)[2] before 2.5 megarad gamma radiation | after 2.5 megarad gamma-radiation |
| --- | --- | --- | --- | --- | --- |
| 13 | 14.83 | — | 0.17 | 15 | 0.18 |
| 14 | 11.83 | 3[3] | 0.17 | 52 | 28 |
| 15 | 12.00 | 3[3] | — | 55 | 26 |
| 16 | 11.00 | 4[4] | — | 32 | 7 |

[1]mean molar weight about 2 × 10⁶ dalton
[2]measured with "viscotester VT-02" by Haake
[3]Bulk density 60 g/l, BET surface 300 m²/g
[4]Bulk density 60 m/l, BET surface 200 m²/g The foregoing mixtures are formed into bandages as in the preceeding examples. They are packed, irradiated with 2.5 megarad gamma rays, and stored. The bandages are in excellent condition, even three months later, both at room temperature and at 40°.

A 37 year old patient, suffering with phlebitis and thrombosis is treated for six months with bandages made from the composition of Example 15. It is found that the bandages are easy to apply, easy to form, had a pleasant odor, and are dry on the surface after 60 to 90 minutes, depending on the relative humidity. The bandages are fully satisfactory in assisting the treatment. The phlebitis recedes, and no skin irritation is observed during treatment. The behavior of the bandage is judged to be excellent by the physician in charge.

EXAMPLE 17

A composition according to the present invention is prepared as follows:
15% zinc oxide (pharmaceutical grade),
25% glycerin, and
11% ethylhydroxyethyl cellulose (viscosity 50 mPas in 2% solution at room temperature)
are stirred successively into 49% water. Bandages are produced with this composition as described in Example 1. They are irradiated with 2.5 megarad gamma rays, constitute good semi-rigid supporting dressings, have a creamy consistency, and are easy to process.

EXAMPLE 18

A composition is prepared by mixing
20% zinc oxide (pharmaceutical grade) and
10% methylhydroxyethyl cellulose (viscosity 40,000 mPas. in 2% solution at room temperature)
into a mixture of 20% glycerin and 50% water. Bandages are produced therefrom in accordance with Example 1, and are irradiated with 3.5 megarad gamma rays. The bandages are found to be completely satisfactory in all respects and substantially in accordance with those produced in the previous examples.

COMPARISON EXAMPLE

In order to demonstrate the effectiveness of the present invention, a prior art bandage is produced from the following composition:
14 g gelatin "Super Platin"
94 g glycerin (99% DAB 8)
92 g zinc oxide (pharmaceutical grade)
400 g distilled water.

The gelatin is carefully stirred into the water, which is previously heated to 70° C. The solution is then cooled under stirring. The other components are stirred in in succession. The zinc oxide paste is applied to a substrate to form a bandage as in the preceeding examples.

The packed bandages are then irradiated with 2.5 megarad gamma rays and the resultant product is examined. It is found that the zinc oxide mass becomes "cheesy" and water can be squeezed out. The bandage can not be used for its intended purpose. The same test is repeated with a commercial zinc oxide bandage, and the same results were obtained.

While only a limited number of specific embodiments of the present invention have been expressly disclosed, it is, nonetheless, to be broadly construed, and not to be limited except by the character of the claims appended hereto.

What we claim is:
1. A bandage comprising a substrate and a composition consisting by weight essentially of
10-35% zinc oxide

2-15% cellulose ether
10-35% glycerin
30-75% water.

2. The bandage of claim 1 wherein said composition consists essentially of
10-20% zinc oxide
3-5% cellulose ether
10-20% glycerin
60-70% water.

3. A bandage of claim 1 which has been subjected to energy-rich radiation.

4. A bandage of claim 3 wherein said radiation is gamma radiation.

5. A method for making the bandage of claim 1 comprising coating said composition onto said substrate.

6. A method of making the bandage of claim 2 which comprises coating said composition onto said substrate.

7. A method according to claim 5 wherein said composition is subjected to energy-rich radiation.

8. A method according to claim 7 wherein said radiation is gamma radiation.

9. A bandage of claim 1 wherein said ether has a viscosity of 50-50,000 mPas in 2% aqueous solution at room temperature.

10. A bandage of claim 9 wherein said viscosity is 50-12,000 mPas.

11. A bandage of claim 10 wherein said viscosity is about 2000 mPas and there is 3-5% of said ether in said composition.

12. A bandage of claim 1 wherein said ether is methylhydroxy ethyl cellulose, ethylhydroxy ethyl cellulose, hydroxypropylmethyl cellulose, methylhydroxypropyl cellulose and mixtures thereof.

13. A bandage of claim 1 wherein said composition has a viscosity of 1-100 Pas.

14. A bandage of claim 1 wherein an inorganic thickener is present.

15. A bandage of claim 14 wherein said thickener is highly dispersed silicon dioxide.

16. A bandage of claim 15 having 2 to 4% by weight of said silicon dioxide.

17. A bandage of claim 1 wherein said substrate is taken from the class consisting of gauze, elastic woven fabric, and non-woven fabric.

18. A bandage of claim 1 wherein said composition is applied in an amount of 120-200 g/m².

19. A bandage of claim 4 wherein said radiation is in an amount of 0.5 to 5 megarad.

20. A bandage of claim 3 wherein said radiation is administered when said bandage is packaged.

21. A bandage of claim 2 wherein
said composition contains 2 to 4% by weight highly dispersed $SiO_2$, has a viscosity of 1 to 100 Pas; said ether having a viscosity, in 2% water solution at room temperature, of 50 to 12,000 mPas., and taken from the class consisting of methylhydroxy ethyl cellulose, ethylhydroxy ethyl cellulose, hydroxypropylmethyl cellulose, methylhydroxypropyl cellulose and mixtures thereof,
said substrate comprising gauze, elastic woven fabric, or non-woven fabric, said substrate being coated on at least one side with 120 to 200 g/m² of said composition,
said bandage having been irradiated with 0.5 to 5.0 megarad of gamma rays after packaging.

22. A method according to claim 6 wherein said composition contains 2 to 4% by weight highly dispersed $SiO_2$, has a viscosity of 1 to 100 Pas.; said ether having a viscosity, in 2% water solution at room temperature, of 50 to 12,000 mPas., and taken from the class consisting of methylhydroxy ethyl cellulose, ethylhydroxy ethyl cellulose, hydroxypropylmethyl cellulose, methylhydroxypropyl cellulose, and mixtures thereof,
coating 120 to 200 g/m² of said composition on a substrate taken from the class consisting of gauze, elastic woven fabric, or non-woven fabric,
packaging said bandage and then irradiating said bandage in said package with 0.5 to 5.0 megarad of gamma rays.

23. A bandage of claim 2 which has been subjected to energy-rich radiation.

24. A bandage of claim 23 wherein said radiation is gamma radiation.

25. A method according to claim 6 wherein said composition is subjected to energy-rich radiation.

26. A method according to claim 25 wherein said radiation is gamma radiation.

27. A bandage of claim 24 wherein said radiation is in an amount of 0.5 to 5 megarad.

28. A bandage of claim 23 wherein said radiation is administered when said bandage is packaged.

* * * * *